(12) United States Patent
Hackenberger et al.

(10) Patent No.: US 9,027,406 B2
(45) Date of Patent: May 12, 2015

(54) TRANSDUCER APPARATUS AND METHOD FOR ASSEMBLING A TRANSDUCER APPARATUS

(75) Inventors: Dane Eugene Hackenberger, Mifflintown, PA (US); Robert Charles Shaffer, Reedsville, PA (US)

(73) Assignee: General Electric Company, Schenectady, NY (US)

( * ) Notice: Subject to any disclaimer, the term of this patent is extended or adjusted under 35 U.S.C. 154(b) by 1031 days.

(21) Appl. No.: 13/108,447

(22) Filed: May 16, 2011

(65) Prior Publication Data
US 2012/0291555 A1  Nov. 22, 2012

(51) Int. Cl.
*G01N 29/28* (2006.01)
*G01N 29/24* (2006.01)

(52) U.S. Cl.
CPC ............ *G01N 29/28* (2013.01); *G01N 29/2493* (2013.01)

(58) Field of Classification Search
CPC . G10K 11/004; G01N 29/225; G01N 29/226; G01N 29/2493; G01N 29/265
USPC .................................... 73/639, 632, 633, 644
See application file for complete search history.

(56) References Cited

U.S. PATENT DOCUMENTS

| | | | | |
|---|---|---|---|---|
| 4,202,216 A | * | 5/1980 | Bull et al. ......................... | 73/639 |
| 4,208,915 A | * | 6/1980 | Edwards ........................... | 73/620 |
| 6,308,570 B1 | * | 10/2001 | Jackson et al. ................... | 73/597 |
| 6,536,553 B1 | * | 3/2003 | Scanlon .......................... | 181/108 |
| 6,688,178 B1 | * | 2/2004 | Schmidt et al. .................. | 73/639 |

FOREIGN PATENT DOCUMENTS

JP          02044247 A    *   2/1990

* cited by examiner

*Primary Examiner* — Laura Martin
*Assistant Examiner* — Rose M Miller
(74) *Attorney, Agent, or Firm* — Hiscock & Barclay LLP

(57) ABSTRACT

According to one aspect of the invention, a transducer apparatus is provided that includes a core section, a transducer disposed in the core section, the transducer configured to transmit or receive signals and a tubular member mounted to the core section for relative rotation, wherein a fluid is disposed in the tubular member. The apparatus further includes a weight reduction device disposed inside the tubular member to occupy a volume inside the tubular member, wherein the weight reduction device is configured to provide a transmission path from the transducer to the tubular member via the fluid.

20 Claims, 3 Drawing Sheets

TRANSDUCER APPARATUS AND METHOD FOR ASSEMBLING A TRANSDUCER APPARATUS

BACKGROUND OF THE INVENTION

The subject matter disclosed herein relates to roller transducers and, in particular, to a weight reduction device for a roller transducer apparatus.

Roller transducers, and specifically ultrasonic roller transducers, may be used to provide an image of a member or part to be inspected for flaws or degradation. For ultrasonic transducers, the cylindrical rotating portion of the apparatus is often filled with a fluid, such as water, wherein the fluid enables communication of ultrasonic signals from a transducer unit within the apparatus to the member being tested. In many instances, the roller transducer is a hand held apparatus that the user manually rolls to produce the image of the member. Due to the weight of the apparatus and the repetitive rolling motion, manual movement of the apparatus can lead to user fatigue and reduced productivity.

BRIEF DESCRIPTION OF THE INVENTION

According to one aspect of the invention, a transducer apparatus is provided that includes a core section, a transducer disposed in the core section, the transducer configured to transmit or receive signals and a tubular member mounted to the core section for relative rotation, wherein a fluid is disposed in the tubular member. The apparatus further includes a weight reduction device disposed inside the tubular member to occupy a volume inside the tubular member, wherein the weight reduction device is configured to provide a transmission path from the transducer to the tubular member via the fluid.

According to another aspect of the invention, method for assembling a transducer apparatus is provided, wherein the method includes forming a weight reduction device having a first density, disposing the weight reduction device on a core section of the transducer apparatus and disposing a tubular member about the weight reduction device. The method further includes disposing a fluid within the tubular member, wherein the fluid has a second density greater than the first density.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
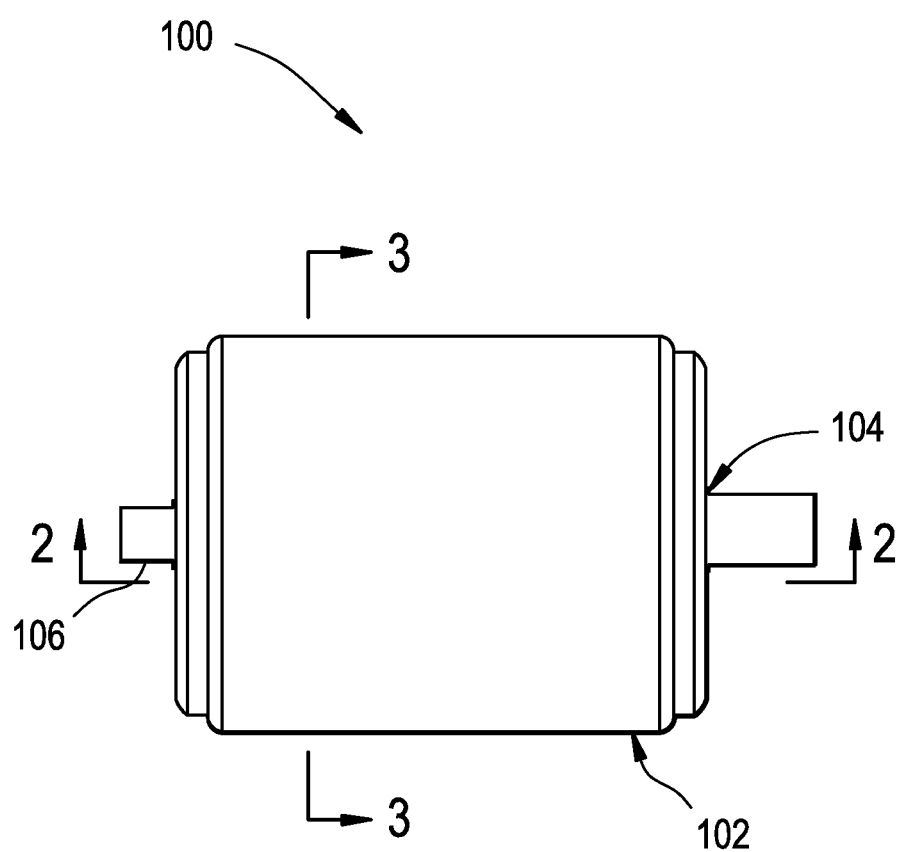
FIG. 1 is a side view of an exemplary roller transducer apparatus.

FIG. 1 is a side view of an exemplary roller transducer apparatus 100. The transducer apparatus 100 includes a tubular member 102 rotatably disposed about or mounted to a core section 104, thereby allowing relative rotation of the tubular member 102. The core section 104 includes an axle 106 configured to be coupled to a frame (not shown) for guiding of the roller transducer apparatus 100 over a material, member or part to be inspected. The frame may be any suitable structure configured to house the tubular member 102 and allow movement of the member relative to the frame. Exemplary frames include a handle to enable manipulation of the transducer apparatus over a surface of the member to be tested. In addition, exemplary frames include suitable electronics and hardware to transmit signals and power to the transducer apparatus, wherein the electronics are coupled via a suitable connection such as via electrical leads at least partially within axle 106 and routed to the core section 104. The exemplary tubular member 102 is mounted to core section 104 for rotation, via a suitable mechanism, and thus enables rotational movement of the tubular member 102 relative to the core section 104 as the transducer apparatus 100 is rolled across the member being tested. In embodiments, the axle 106 is coupled to the frame and the core section 104 while the tubular member 102 is coupled to the core section 104 by a suitable device, such as a bearing assembly, to allow the tubular member 102 to rotate.

The transducer apparatus 100 includes an ultrasonic transducer, associated hardware and circuitry configured to provide information about the condition or character of the member by transmitting ultrasonic acoustic waves into the object and detecting reflections (or "echos") of the waves from within the member. In a transducer system, a electronics and associated hardware may be coupled to the transducer apparatus 100 to send, receive and process signals corresponding to the detected ultrasonic acoustic waves. Further, software and/or firmware may run on the electronics to analyze the waves and to determine if there are imperfections or flaws in the test member. By transmitting an ultrasonic wave of known characteristics (i.e., frequency, amplitude, etc.) through the member, the system is able to detect anomalies by analyzing a change of the wave as it is reflected through the member. In one exemplary embodiment, the transducer apparatus 100 is manually rolled over airplane parts to inspect the parts for flaws, material delamination and/or material degradation. In other embodiments, the transducer apparatus 100 includes other suitable transducers for non-destructive part inspection, such as electromagnetic sensors.

Figure 2:
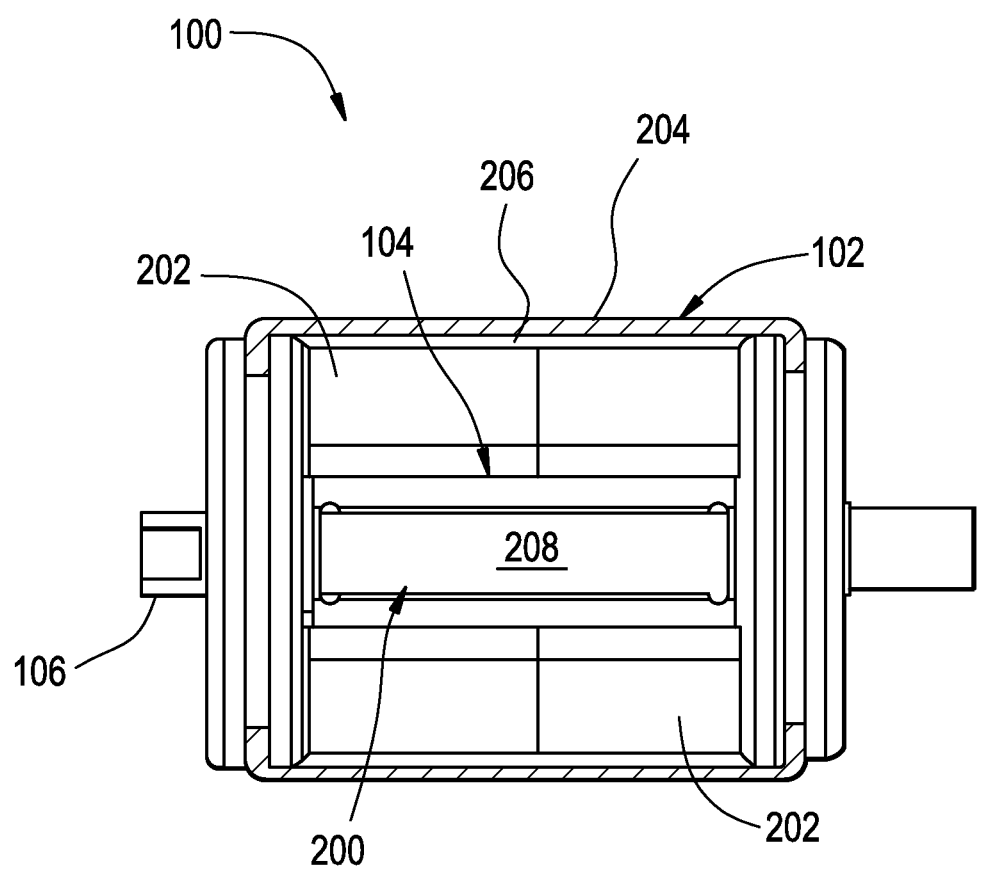
FIG. 2 is a sectional side view of the exemplary roller transducer apparatus taken approximately along lines 2-2 in FIG. 1.

FIG. 2 is a sectional side view of the exemplary roller transducer apparatus 100. The transducer apparatus 100 includes a transducer 200 (or "transducer unit") in the core section 104 and a weight reduction device 202 disposed about most of the core section 104. The tubular member 102 is disposed about the weight reduction device 202 and includes a wall 204. A fluid is disposed in a cavity 206 within the tubular member 102, wherein the fluid is suitable for communication of ultrasonic acoustic waves to and from a face 208 of the transducer 200. In an embodiment, the tubular member 102 comprises a substantially flexible and hollow tubular member, wherein at least a portion of the tubular member is flexible. The flexible portion of the tubular member 102 may be referred to as a tire. In another embodiment, the tubular member 102 is substantially rigid. Similar to a tire for a vehicle, a contact patch is created as the cylindrical member is rolled across the member to be tested. The contact patch provides a surface area into which to transmit the ultrasonic waves to test the member. The fluid and the surfaces defining the cavity 206 of the cylindrical member defines a transmission path for the ultrasonic waves with minimal distortion.

At least a portion of the exemplary tubular member 102 comprises a suitable elastic material, such as an elastomer, urethane or rubber. In other embodiments, the tubular member 102 may be a multi-sided member (e.g., a 6-16 sided member) configured to enable rolling across a surface to be inspected. The fluid disposed within the tubular member 102 and cavity 206 is a suitable jelly, oil or liquid, such as a water solution or water. The transducer 200 includes suitable circuitry to transmit and receive ultrasonic acoustic waves. An exemplary transducer 200 includes an array of ultrasonic transducers, wherein the array of transducers is arranged to transmit and/or receive ultrasonic waves in a selected pattern. Further, the array of transducers may be multiplexed and/or focused on a selected portion of the test member using phased array techniques.

The weight reduction device 202 is configured to displace a portion of the fluid that may be contained within the tubular member 102. The overall density of the weight reduction device 202 is less than the density of the fluid, thereby reducing the overall weight of the transducer apparatus 100. Therefore, the weight reduction device 202 is disposed inside the tubular member 102 to occupy a volume inside the tubular member 102 to displace fluid that would otherwise occupy that volume. In one embodiment, the weight reduction device 202 comprises a substantially hollow sealed member filled with a gas, such as air. The weight reduction device 202 may be formed from one or more parts of a durable light weight material, such as a plastic or polymer material. In other embodiments, the weight reduction device 202 comprises a substantially solid light weight composite, polymer or closed cell foam.

Figure 3:
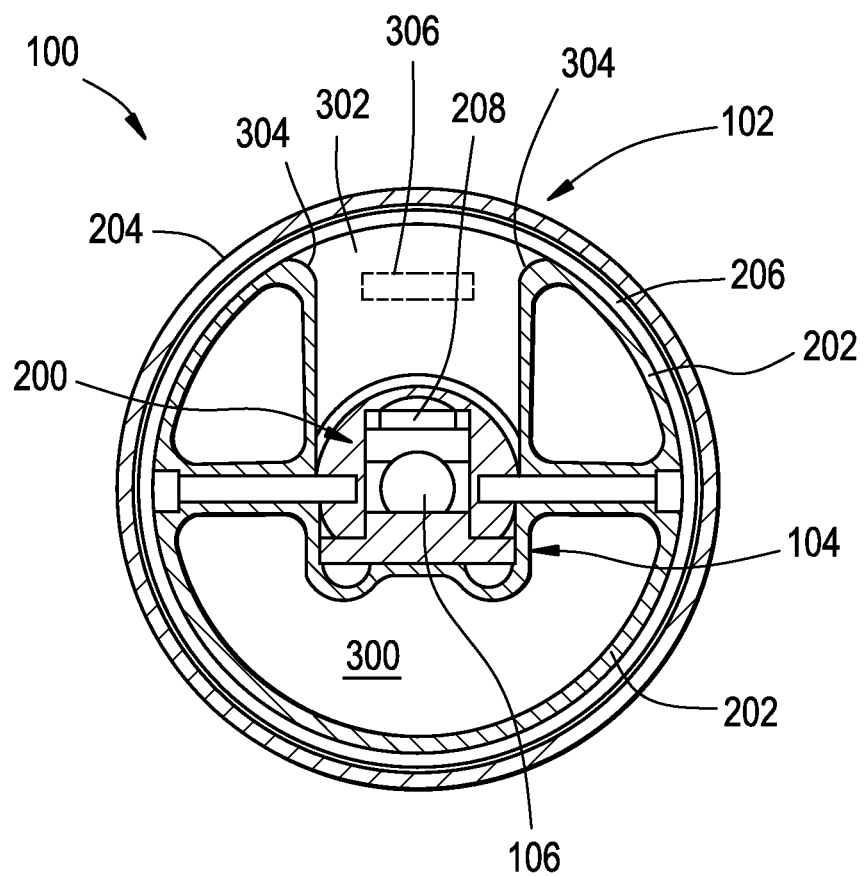
FIG. 3 is a sectional end view of the exemplary roller transducer apparatus taken approximately along lines 3-3 in FIG. 1.

The weight reduction device 202 has a suitable geometry to expose at least a portion of the transducer face 208, thereby allowing transmission of acoustic waves through the fluid disposed in the tubular member 102. As shown in FIG. 3, the exemplary geometry of the weight reduction device 202 comprises a substantially C shaped cross section. Other geometries for the weight reduction device 202 may include a V shape, a half circle or any other suitable geometry to enable signal transmission from the transducer 200 inside the tubular member 102 while reducing the amount of fluid within the transducer apparatus 202. In embodiments, the geometry of the weight reduction device 202 may be selected based on application-specific details, such as rolling speed during inspection, testing member surface characteristics or apparatus orientation during use. The weight reduction device 202 is coupled to a stationary portion of the core section 104, wherein the stationary portion includes the transducer 200 and axle 106. Thus, in one embodiment, the weight reduction device 202 is stationary with respect to the transducer 200 to ensure unblocked transmission of acoustic signals to and from the transducer to the member being inspected. In other embodiments, the weight reduction device 202 is floating or non-stationary with respect to the transducer 200.

The weight reduction device 202 includes a hollow portion or cavity 300 that may be filled with a gas or suitable light weight material. In addition, the weight reduction device 300 may have a vacuum applied to the cavity 300 to remove at least a portion of the gas within the device to further reduce weight. The depicted weight reduction device 202 is coupled to a non-rotating part the core section 104 and is configured to expose at least a portion of the transducer face 208, thereby enabling communication of acoustic signals through the fluid disposed in a cavity 302 in the weight reduction device 202. Accordingly, the arrangement enables transmission of acoustic signals from the transducer 200 along cavity 302 to an inner surface of the wall 204 via the fluid. The walls forming the cavity 302 may be parallel or may be at an angle relative to one another. The geometry and cavity depth of cavity 302 may be altered, depending on the application and the desired acoustic path, to reduce interference and reflections of ultrasonic wave transmissions. The exemplary weight reduction device 202 includes radii 304 configured to enable fluid communication along the cavity 206 between the device and tubular member 102 when the tubular member 102 deforms as it is pressed against a surface of the test member. The radii 304 enable rolling movement of the deformed member without interference between the weight reduction device 202 and the tubular member 102. As depicted, fluid is disposed in cavities 206 and 302 about the weight reduction device 202, wherein the tubular member 102 is substantially encapsulates the device, thus sealing the fluid within the apparatus as the tubular member 102 rotates about the core section 104 and transducer 200.

In one embodiment a portion of the transducer 200 and core section 104 may extend into the cavity 302 to a position 306, wherein the distance between the position 306 and the wall 204 is reduced, thereby providing a shorter transmission path for the ultrasonic waves. When at least a portion of the transducer 200 is in position 306, the weight reduction device 202 may be placed opposite the transducer face 208 to further reduce weight in the apparatus. In embodiments, the weight reduction device 202 is floating relative to the core section 104 and includes a geometry and/or weighting to maintain alignment with respect to the core section 104 to provide a transmission path and exposure for the transducer face 208.

In embodiments, the lower density of the weight reduction device 202, relative to the fluid (e.g. water), reduces the weight of the transducer apparatus 100 by about 10% to about 80%, depending on dimensions of the apparatus and materials used. An exemplary apparatus with a diameter of about 2 to about 5 inches may have a weight reduction of about 10% to about 30% as compared to device without the weight reduction device. An exemplary apparatus with a diameter of about 10 to about 16 inches may have a weight reduction of about 50% to about 80% as compared to device without the weight reduction device. Thus, the reduced weight of the transducer apparatus 100 increases productivity, efficiency and safety, and ergonomic utility of the inspection processes using the apparatus.

Exemplary steps in making the transducer apparatus 100 may include the following. Placing the transducer 200 on a frame of the apparatus. Disposing the weight reduction device 202 about the transducer, wherein the weight reduction device 202 exposes the transducer face 208 to provide a transmission path to and from the face. Placing the tubular member 204 about the weight reduction device 202, wherein at least a portion of the tubular member 204 is flexible to allow rolling of the tubular member 204 over a surface of the test member. Further, the tubular member 204, weight reduction device 202 and transducer 200 are arranged to provide the transmission path from the transducer face 208 directly to the surface of the test member. Finally, a fluid is disposed within the tubular member 204 and around the weight reduction device 202, wherein the fluid allows transmission of the ultrasonic waves without substantial reflectance or obstruction.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. An ultrasonic transducer apparatus comprising:
a core section;
an ultrasonic transducer disposed in the core section, the ultrasonic transducer configured to transmit or receive signals;
a tubular member mounted to the core section for relative rotation;
a fluid disposed in the tubular member; and
a weight reduction device disposed inside the tubular member to occupy a volume inside the tubular member, wherein the weight reduction device is configured to provide a transmission path from the ultrasonic transducer to the tubular member via the fluid;
wherein the weight reduction device is configured to encompass at least a portion of the ultrasonic transducer.

2. An ultrasonic transducer apparatus comprising:
a core section;
an ultrasonic transducer disposed in the core section, the ultrasonic transducer configured to transmit or receive signals;
a tubular member mounted to the core section for relative rotation;
a fluid disposed in the tubular member; and
a weight reduction device disposed inside the tubular member to occupy a volume inside the tubular member, wherein the weight reduction device is configured to provide a transmission path from the ultrasonic transducer to the tubular member via the fluid, wherein the weight reduction device is configured to encompass at least a portion of the core section.

3. The apparatus of claim 2, wherein the weight reduction device is coupled to a stationary portion relative to the core section.

4. The apparatus of claim 3, wherein the tubular member is configured to rotate about the weight reduction device and the core section.

5. The apparatus of claim 2, wherein the tubular member comprises a substantially flexible and hollow tube.

6. The apparatus of claim 2, wherein the weight reduction device has a first density and the fluid has a second density, wherein the first density is less than the second density.

7. The apparatus of claim 2, wherein the weight reduction device is configured to expose a face portion of the ultrasonic transducer.

8. The apparatus of claim 2, wherein the weight reduction device comprises a substantially hollow polymer member.

9. The apparatus of claim 2, wherein the weight reduction device reduces an overall weight of the apparatus by at least about 10% as compared to an apparatus without the weight reduction device.

10. An ultrasonic transducer apparatus comprising:
a core section;
an ultrasonic transducer disposed in the core section, the ultrasonic transducer configured to transmit or receive signals;
a tubular member mounted to the core section for relative rotation;
a fluid disposed in the tubular member; and
a weight reduction device disposed inside the tubular member to occupy a volume inside the tubular member, wherein the weight reduction device is configured to provide a transmission path from the ultrasonic transducer to the tubular member via the fluid, wherein the weight reduction device has a substantially C-shaped cross section.

11. An ultrasonic transducer apparatus comprising:
a core section;
an ultrasonic transducer disposed in the core section, the ultrasonic transducer configured to transmit or receive signals;
a tubular member mounted to the core section for relative rotation, wherein a fluid of a first density is disposed in the tubular member; and
a weight reduction device disposed inside the tubular member to occupy a volume inside the tubular member, wherein the weight reduction device has a second density less than the first density and is configured to provide a transmission path from the ultrasonic transducer to the tubular member via the fluid, wherein the weight reduction device confines the fluid to a cavity, the cavity defined by radii of the weight reduction device.

12. The apparatus of claim 11, wherein the weight reduction device is coupled to a stationary portion of the core section.

13. The apparatus of claim 11, wherein the tubular member comprises a substantially flexible and hollow tube.

14. The apparatus of claim 11, wherein the weight reduction device comprises a substantially hollow polymer member.

15. The apparatus of claim 11, wherein the weight reduction device is disposed on the core section to expose a face portion of the ultrasonic transducer.

16. The apparatus of claim 11, wherein the weight reduction device is disposed on the core section and configured to provide a transmission path from the ultrasonic transducer to the tubular member via the fluid.

17. An ultrasonic transducer apparatus comprising:
a core section;
an ultrasonic transducer disposed in the core section, the ultrasonic transducer configured to transmit or receive signals;
a tubular member mounted to the core section for relative rotation, wherein a fluid of a first density is disposed in the tubular member; and
a weight reduction device disposed inside the tubular member to occupy a volume inside the tubular member, wherein the weight reduction device has a second density less than the first density and is configured to provide a transmission path from the ultrasonic transducer to the tubular member via the fluid, wherein the weight reduction device comprises a substantially C-shaped cross section.

18. A method for assembling an ultrasonic transducer apparatus, the method comprising:
forming a weight reduction device having a first density;
disposing the weight reduction device on a core section of the ultrasonic transducer apparatus such that the weight reduction device encompasses at least a portion of the core section;
disposing a tubular member about the weight reduction device; and disposing a fluid within the tubular member, wherein the fluid has a second density greater than the first density.

19. The method of claim 18, wherein the disposing the weight reduction device comprises orienting the weight reduction device on the core section to provide a transmission path from the ultrasonic transducer to the tubular member via the fluid.

20. The method of claim 18, wherein forming the weight reduction device comprises molding a hollow polymer member.

* * * * *